United States Patent [19]

Goodson et al.

[11] 4,324,858
[45] Apr. 13, 1982

[54] STABILIZATION OF CHOLINESTERASE, DETECTOR KIT USING STABILIZED CHOLINESTERASE, AND METHODS OF MAKING AND USING THE SAME

[75] Inventors: Louis H. Goodson, Kansas City, Mo.; Alan Goodman, Edgewood, Md.

[73] Assignee: Midwest Research Institute, Kansas City, Mo.

[21] Appl. No.: 160,027

[22] Filed: Jun. 16, 1980

[51] Int. Cl.³ .............................................. C12Q 1/46
[52] U.S. Cl. ..................................... 435/20; 435/179; 435/805; 435/810
[58] Field of Search .................. 23/230 B; 422/56, 57; 435/4, 20, 176, 177, 179, 180, 184, 188, 196, 197, 805, 810

[56]  References Cited
U.S. PATENT DOCUMENTS

| | | | |
|---|---|---|---|
| 3,049,411 | 8/1962 | Gelman et al. | 435/20 |
| 3,378,463 | 4/1968 | Guilbault et al. | 435/20 |
| 3,515,644 | 6/1970 | Kramer et al. | 435/20 |
| 3,526,480 | 9/1970 | Findl et al. | 422/66 |
| 3,539,452 | 11/1970 | Penicnak | 435/20 |
| 3,689,224 | 9/1972 | Agnew et al. | 435/20 |
| 3,715,298 | 2/1973 | Goodson et al. | 435/20 |
| 3,730,841 | 5/1973 | Salvatore et al. | 435/182 |
| 3,741,876 | 6/1973 | Guilbault et al. | 435/20 |
| 3,809,616 | 5/1974 | Schmitt et al. | 435/20 |
| 4,059,491 | 11/1977 | Iwasa et al. | 23/230 B |

OTHER PUBLICATIONS

Makinen, et al., "Reactivity and Cryoenzymology of Enzymes in the Crystalline State," *Ann. Rev. Biophys. Bioeng.* 1977, pp. 301–315.

*Primary Examiner*—Peter A. Hruskoci
*Attorney, Agent, or Firm*—Merchant, Gould, Smith, Edell, Welter & Schmidt

[57]  ABSTRACT

The stability of a cholinesterase (particularly a cholinesterase solution impregnated into a porous material and air-dried) can be improved by: (a) buffering the cholinesterase solution with a zwitterionic buffer, e.g. a buffer having a sulfonic acid group and a protonatable amine group, and, preferably, (b) further drying the impregnated, air-dried porous material under a high vacuum (e.g. 0.01 mm Hg or less) at normal ambient temperatures. The most useful porous materials are sheet-like in nature; that is, they have only two major surfaces. An impregnated, sheet-like material of this invention can be used in a cholinesterase inhibitor detector kit. A typical kit of this type provides a simple means for detecting, inter alia, environmental cholinesterase-inhibiting pollutant, e.g. organophosphorous pesticides and nerve agents.

19 Claims, No Drawings

STABILIZATION OF CHOLINESTERASE, DETECTOR KIT USING STABILIZED CHOLINESTERASE, AND METHODS OF MAKING AND USING THE SAME

TECHNICAL FIELD

This invention relates to a method for stabilizing a cholinesterase. An aspect of this invention relates to a method for providing a porous material impregnated with substantially stabilized cholinesterase and a method for utilizing this porous material in a kit for detecting anticholinesterase compounds. Still another aspect of this invention relates to the anticholinesterase detector kit and methods for using it. Still another aspect of this invention relates to a method for detecting environmental or ambient cholinesterase inhibitors in food, water, soil, air, etc.

PRIOR ART

For the last several years, there has been increasing concern regarding the presence of a variety of pollutants in the environment. Several of these pollutants have an important property known as cholinesterase inhibition, i.e. the ability to inhibit the catalytic action of the class of enzymes referred to as "cholinesterase". It has long been recognized that cholinesterase inhibitors can be detected by simple, highly sensitive devices and techniques. Accordingly, it has been found to be unnecessary to utilize complicated chemical analytic techniques to detect the presence of these pollutants or toxic agents—the aforementioned simple devices, disclosed in detail in the scientific and patent literature, have the ability to indicate the presence of miniscule amounts of these agents or pollutants. For example, the detection sampler described by Agnew et al in U.S. Pat. No. 3,689,224, issued Sept. 5, 1972 is said to be suitable for rapidly testing for contaminants such as nerve gases or agents. The Agnew et al sampler includes a pad impregnated with an enzyme such as a serum cholinesterase and a pad impregnated with a dye-forming ester such as indoxyl acetate. When the two pads are brought together so that the cholinesterase can contact the indoxyl acetate, the indoxyl acetate is hydrolyzed, causing a color change. However, the presence of even a minute amount of some cholinesterase inhibitor will inhibit this reaction and prevent the color change. Thus, the color change indicates a normal, essentially pollution-free situation, while a lack of color change indicates the presence of a cholinesterase inhibitor.

In its strictest sense, a "cholinesterase" or "acetyl cholinesterase" enzyme is specific for esters of choline, e.g. acetyl choline. However, in the art of anticholinesterase agent detection, the term "cholinesterase" is used somewhat more broadly to include substances such as horse serum cholinesterase which will catalyze the hydrolysis of a variety of esters in addition to acetyl choline, hence the ability of the person skilled in the art to select suitable ester-type substrates for the enzyme, which substrates will provide a simple indication of enzyme inhibition or lack of inhibition. As noted previously, one of the simplest types of indication is a color change (or lack of color change) readily apparent to the human eye. For this reason, the chromogenic ester-type substrate is sometimes referred to as a developing reagent. In the case of indoxyl acetate or other indoxyl esters, the active enzyme hydrolyzes the ester to a fluorescent indoxyl derivative which is then oxidized to a colored species. If a ferro/ferricyanide system is present, the color change is accelerated. A perceptible color change can develop in a matter of seconds, e.g. 7–30 seconds; see U.S. Pat. No. 3,049,411 (Gelman et al), issued Aug. 14, 1962.

Several cholinesterases are commercially available, typically from animal or marine sources such as horse serum, electric eels, bovine erythrocytes, and the like. Fully effective large-scale commercialization of cholinesterase/hydrolyzable ester detector kits and techniques have nevertheless been hampered by the relative instability of cholinesterases and cholinesterase solutions. For example, eel cholinesterase solutions begin to deteriorate at normal ambient temperatures within a matter of hours. Perhaps for this reason, prior art detector kits typically do not utilize water solutions or dispersions of cholinesterase enzymes but rather the impregnated porous materials of the type generally described in the aforementioned Gelman et al patent, the pad described in the aforementioned Agnew et al patent, the dual substrate system described in U.S. Pat. No. 3,515,644 (Kramer et al), issued June 2, 1970, the polymeric materials described in U.S. Pat. No. 3,809,616 (Schmitt et al), issued May 7, 1974, the enzyme pad containing immobilized cholinesterase described in Example 2 of U.S. Pat. No. 3,715,298 (Goodson et al), issued Feb. 6, 1973, the carrier described in U.S. Pat. No. 3,730,841 (Salvatore et al), issued May 1, 1973, and the like. See also U.S. Pat. No. 3,741,876 (Guilbault et al), issued June 26, 1973 and U.S. Pat. No. 3,378,463 (Guilbault et al), issued Apr. 16, 1968. Another common practice is to buffer the cholinesterase solutions before impregnating the pad or other porous material. Like most enzymes, the cholinesterases having a pH range in which maximum activity occurs (e.g. from about 6 to about 9), and a suitable pH range can also facilitate the aforementioned color change.

Through the various techniques described in the prior art, some improvement in, for example, bovine red cell cholinesterase stability has been obtained. Gelman et al (U.S. Pat. No. 3,049,411) disclose retention of activity for "extended" periods of time a 65° C. for an unspecified cholinesterase. In actual practice, however, it is difficult to obtain a sensitive, simple, portable, economical kit or method for the rapid detection of toxic levels of agents or pollutants which inhibit cholinesterase without resorting to cumbersome steps for the improvement of shelf life, e.g. refrigeration. That is, the present state of the art has not solved all the problems of enzyme stability, particularly for simple detector kits or samplers of the type disclosed in the aforementioned Agnew et al patent, and particularly when the enzyme is eel cholinesterase. Complex devices of the type disclosed in, for example, Findl et al, U.S. Pat. No. 3,526,480, issued Sept. 1, 1970 and relatively complex techniques of the type disclosed by Guilbault et al, U.S. Pat. No. 3,378,463, issued Apr. 16, 1968 may be well-suited to technically trained personnel, but simpler techniques and devices are desirable for users having little or no technical experience and no available instrumentation other than the kit or samplers. Furthermore, eel cholinesterase offers the advantage of greater sensitivity to toxic compounds of the organophosphorus type (as compared to horse serum and bovine erythrocyte cholinesterase) but this advantage is not available for utilization in these kits or samplers, due to the greater instability of this particular cholinesterase.

SUMMARY OF THE INVENTION

It has now been found that a cholinesterase (particularly eel cholinesterase) can be stabilized by drying conditions sufficient to remove substantially all physically bound water and thereby produce a dried enzyme having substantially no measurable water vapor pressure in a closed system. It has further been discovered that zwitterionic buffers can make a significant contribution to the stability and/or chromogenic activity of the cholinesterase.

Briefly, this invention involves stabilizing a cholinesterase (preferably electric eel cholinesterase) by a method including the steps of:

(a) uniformly distributing (i.e. dissolving or dispersing) the cholinesterase through a buffered aqueous medium, the preferred buffer comprising a zwitterionic compound;

(b) impregnating a porous material with the cholinesterase-containing aqueous medium, and (c) drying the impregnated porous material, preferably by subjecting the resulting impregnated porous material to a partial vacuum (preferably a very high vacuum) in a zone of subatmospheric pressure and generally normal ambient temperatures.

The degree of vacuum in the zone of subatmospheric pressure can be determined in any of the common units of measure, e.g. inches or millimeters of mercury (in. or mm Hg), atmospheres, pascals, etc. A vacuum of less than one mm Hq (less than about 0.001 atmospheres) is normally needed to achieve sufficient desiccation of the dried enzyme. To insure adequate drying, the subatmospheric zone need not contain a desiccating agent, but such agents can be included if desired. Preferred zwitterionic buffering compounds have functional groups of the sulfonic acid and protonatable amine type, i.e. aminosulfonic acids which, by virtue of their ionizable proton and their protonatable (primary, secondary, or tertiary) amine are capable of forming an internal salt.

The treated or impregnated porous material made according to this invention can be utilized in detector kits for sensing minute quantities of anticholinesterase agents or pollutants. Typically, these kits include a second porous material treated or impregnated with an ester which can serve as the enzyme substrate or developing agent. Preferably, the two treated porous materials are included in the same package, which package is provided with a barrier for preventing cholinesterase inactivation by sublimation of the substrate during storage. Accordingly, the usual practice is to package the substrate-treated material in a sealed packet. When a test for an anticholinesterase compound is desired, the enzyme and anticholinesterase compound are incubated for a fixed time; the barrier is removed; and conditions for the hydrolysis of the ester are provided. For example, the two porous materials can be brought into contact. To facilitate the enzymatic hydrolysis, moisture can be deliberately added to one or both of the porous materials. A cholinesterase-inhibiting amount of anticholinesterase agent (e.g. a toxic substance such as an organo-phosphorous pesticide) can prevent the color change normally wrought by contact between cholinesterase and indoxyl esters in the presence of moisture. Thus the lack of a color change can be a very sensitive indication of the presence of ambient or environmental pollution or contamination by such toxic substances.

DETAILED DESCRIPTION

Many of the materials used in this invention have been commercially available for several years, including the electric eel cholinesterase, zwitterionic compounds such as the aminosulfonic acids, silica gel papers, laminated foil plastic packaging materials, etc. Cholinesterases can be obtained in commercial quantities in a refrigerated state and stored over a desiccant in a freezer for a significant period of time without excessive loss of activity. Eel cholinesterase as received from a commercial supplier is reported to survive for 6 months if stored in this manner. A cholinesterase-treated porous material of this invention, suitably desiccated and sealed in a protective package has been found to retain adequate cholinesterase activity for five days at 90° C., which is believed to be equivalent to five years storage at normal ambient temperatures (e.g. 10°–35° C.). By contrast, an aqueous solution of eel cholinesterase is stable for only a few hours at 25° C. The high retention of cholinesterase activity provided by this invention is considered to make practical the use of the familiar cholinesterase/ester-developer reaction in a wide variety of environmental and industrial monitoring problems, e.g. the monitoring of air, water, soil, and food for pesticide residues and the like. A principal utility for the detector or sampler kits of this invention lies, however, in the field of detecting the presence of those carbamate, organo-sulfur, and organo-phosphorus compounds having anticholinesterase activity, as well as the classic cholinesterase inhibitors such as eserine. Both the "specific" and "nonspecific" or "pseudo" cholinesterases are inhibited in much the same manner by these carbamate, organo-S, and organo-P compounds, but different cholinesterases exhibit different degrees of sensitivity to these various compounds. For example, eel cholinesterase is particularly sensitive toward various organo-phosphorus "nerve agents" or "nerve gases".

Since the degree of cholinesterase inhibition varies with the different types of cholinesterase, the best sensitivity is usually obtained by matching enzyme and inhibitor on a case-by-case basis.

Among the more significant environmental pollutants which can be monitored by this invention are the phosphonofluoridates, the phosphoramidocyanidates, the alkyl condensed phosphate esters such as the alkyl pyrophosphates, the aromatic thiophosphates (including nitrophenyl thiophosphates), the phosphorothioates, the vinyl phosphates, the so-called nerve gases, and the aforementioned carbamates. More specifically, these pollutants include i-propyl methylphosphonofluoridate, ethyl dimethylphosphoramidocyanidate, pinacolyl methylphosphonofluoridate, cyclohexyl methylphosphonofluoridate, tetraethyl pyrophosphate, diethyl p-nitrophenyl thiophosphate ("Parathion"), O,O-diethyl 2ethyl thioethyl phosphorothioate ("Systox"), and dimethyldichlorovinyl phosphate (DDVP), as well as the other compounds mentioned previously. These types of compounds are sometimes better known by trademarks and coined names such as "Diazinon", "Sevin", "Carbofuran", "Malathion", "Azodrin", "Disulfoton", "Guthion", ∓Trithion", "Mesurol", "Baygon", "Paraoxon", "Monitor", "Dursban", "Gardona", "Dasanit", "Dylox", "Soman", "Tabun", "VX", "Vapora", "Sarin", "GD", "GP", etc.

The preferred ester substrates or developers for the cholinesterase are also well known. Acetyl choline can, of course, be a substrate. For easy use in a detector kit, indoxyl esters (particularly the lower alkanoyl and thioalkanoyl esters) and indophenyl esters (e.g. dichloroindophenyl alkanoyl esters) are preferred. The indoxyl esters provide good results in combination with eel cholinesterase, and the indophenyl esters are particularly effective with horse serum cholinesterase. The indoxyl esters may be N-substituted as in U.S. Pat. No. 3,741,876 (the Guilbault et al patent cited previously). U.S. Pat. No. 3,378,463 (Guilbault et al, also cited previously) reports the resorufin esters can be used as substrates. The substrate or developer is preferably used with a ferro/ferricyanide redox system.

The preferred buffers are zwitterionic and capable of forming internal salts. The proton-supplying substituent of these buffers is preferably a sulfonic acid group ($-SO_3H$), and the preferred proton acceptor is a primary, secondary, or tertiary amine. The water solubility of the buffer is preferably sufficient to provide a 0.01 molar solution. Optimum results are obtained with a 0.05–1.0 M solution, e.g. 0.5 M. The protonatable amine group can be alpha, beta, gamma, etc. with respect to the sulfonic acid group, consistent with adequate steric accessibility of the two (or more) substituents of the internal salt-forming group. The amine group can be aliphatic (including substituted aliphatic), carbocyclic or heterocyclic aliphatic (e.g. cycloaliphatic, morpholino, piperazino, etc.) or aromatic in nature, the aromatic amines being less preferred due to delocalization of the electron pair on the amine.

Thus, typical zwitterionic buffers used in this invention have the formula

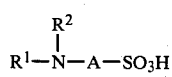

wherein A represents a divalent aliphatic (including substituted aliphatic, e.g. hydroxy-aliphatic), cycloaliphatic, or (less preferably) aromatic residue, and $R^1$ and $R^2$ are the same or different and represent aliphatic (including substituted aliphatic such as hydroxyaliphatic), carbocyclic or heterocyclic aliphatic, e.g. morpholino, piperazino, etc., or (less preferably) aromatic groups, or $R^1$ and $R^2$ can together constitute the residue of a carbocyclic or heterocyclic cycloaliphatic or (less preferably) aromatic ring. For example, $R^1$ and $R^2$ can constitute the residue of a 5- or 6-member carbocyclic ring or heterocyclic ring such as morpholine or piperazine ring. The other heterocyclic nitrogen on the piperazine ring can be N-substituted with an $-A'-SO_3H$ substituent, wherein $A'$ represents the same type of divalent residue as A.

Piperazine sulfonic acids, including piperazine-N,N'-bis-aliphatic sulfonic acids such as piperazine-N,N'-bis-(omega-alkane sulfonic acid) and (omega-hydroxyalkane sulfonic acid) are among the preferred buffers. Both 1,4-bis(3-sulfopropyl)piperazine and 1,4-bis(3-sulfo-2-hydroxypropyl) piperazine are particularly preferred for use in this invention, since they impart (individually or in combination) a high degree of stability to the eel cholinesterase enzyme. Other 2-hydroxypropane sulfonic acids which are 3-substituted with an amine group are commercially available, e.g. the 3-(N-morpholino), 3[N-bis(hydroxyethyl)aminol], and 3(N-piperzine, N'-hydroxyethyl) analogs. These provide some stabilization also. Another suitable class of buffers includes mono-aminoalkyl sulfonic acids substituted with the tris(hydroxymethyl) methyl group, e.g. N-tris(hydroxymethyl) methyl-2-aminoethane sulfonic acid. Since the maximum activity of the enzyme occurs generally within the pH range of about 6 to about 9, one purpose of these buffers is to stabilize the pH of the enzyme-containing impregnation solution or dispersion. Another purpose of the buffer is to stabilize the pH in a range which facilitates the color change reaction which occurs when the indoxyl ester or other ester developer or substrate is hydrolyzed.

A common practice in the prior art is to use a combination of an amine and a phosphate as a buffering system. For reasons which are not readily apparent, there is an advantage in replacing such a system with a zwitterionic compound. The mechanism by which zwitterionic compounds make a greater contribution to the stability of the enzyme is not presently understood.

As is known in the art, a particularly convenient way to provide a source of cholinesterase for use in an anti-cholinesterase detector kit involves impregnating a porous pad or sheet-like material with an aqueous medium containing the cholinesterase and then drying the resulting impregnated porous material. The pad or sheet-like material or web can be microporous or macroporous and can include materials such as the enzyme paper described in U.S. Pat. No. 3,049,411 (cited previously), column 2, lines 16–20. As noted in the U.S. Pat. No. 3,049,411, other porous supports, such as organic and glass fibrous mats and silica gel may be substituted for the filter paper. Silica gel paper can be included with the enzyme paper as an additional element of the kit package. This additional element can serve as a desiccant. A suitable silica gel paper is commercially available under the trademark "PROTEK-SORB". Suitable types of absorbents or adsorbents for the enzyme include ion exchange paper (e.g. diethylaminoethyl cellulose ion exchange paper), cellulose paper, filter paper, webs or bats of synthetic fibers, membranes, and the like. Cationic ion exchange paper appears to assist in providing the fastest and most readily observable response in the aforementioned color-change reaction.

Buffer solutions prepared according to this invention generally comprise water, the zwitterionic agent, pH-adjusting agents (e.g. mineral acids or bases), and, if desired, surface active agents and various conventional ingredients. The activity of the enzyme added to this buffer solution can be determined by any suitable conventional technique or assay. The total units of enzyme in a solution will be determined by the number of milligrams of enzyme used to make the solution multiplied by the assayed activity in units/mg. Enzyme activity in units/mg can be calculated by a manual method or automatically using a programmable calculator. Enzyme activity is determined by:

$$\text{Units/mg} = \frac{(\text{ml NaOH/min}) \times (M \text{ NaOH} \times 10^3)}{\text{enzyme conc. (mg/ml)} \times (\text{ml of enzyme solution added})}$$

The above expression is based upon an enzyme solution analysis in which a standardized acetylcholine chloride solution at a buffered pH of 8.0 is blended with an eel cholinesterase solution buffered according to this invention. A hydrolysis is thereby initiated, and the rate of hydrolysis can be determined by titration with a standardized sodium hydroxide solution as described subsequently.

The Vacuum-Assisted Drying Step

The preferred method of drying a cholinesterase enzyme according to this invention involves subjecting the previously described impregnated porous material (i.e. the porous material impregnated with the buffered cholinesterase solution or dispersion) to a high degree of vacuum in a zone of subatmospheric pressure and generally normal ambient temperatures. Although this invention is not bound by any theory, it is believed that conventional drying techniques (e.g. air drying at 25° C. for 2 or 3 hours) are not adequate, even in the presence of some desiccants, to remove sufficient water from the enzyme itself. It is presently believed that the conventional airdrying step crystallizes the cholinesterase enzyme, resulting in an open, ordered array of enzyme molecules having discrete sits of intermolecular contact. This array of molecules is believed to include interstitial regions which can amount to a significant portion of the crystal volume and can be occupied by water molecules left over from the bulk water solvent. These solvent water molecules may be present in addition to any bound water and may provide large solvent channels through which diffusion of substrates and products may occur, thereby making possible the continued activity of the enzyme even in the crystalline state. Not all enzymes and proteins retain enzymatic or functional reactivity in the crystalline state, but it is presently believed that the commercially available types of cholinesterase do have this crystalline state activity. Accordingly, it is believed that the drying under high vacuum conditions reduces significantly the residue of solvent water molecules in the crystalline enzyme structure, thereby helping the enzyme to retain its sterospecific integrity and making the enzyme more resistant to deterioration until use of the enzyme in an analytical test is desired. Wetting of the porous material containing the vacuumdried, crystallized enzyme restores full activity and permits the use of the enzyme in anticholinesterase detection.

According to Makinen et al, Ann Rev. Biophys. Bioeng. 6:301 (1977), at page 308, crystalline globular proteins are generally considered to form the aforementioned open ordered array of molecules upon crystallization. Makinen et al report that about half of the crystal volume is occupied by bulk solvent. Again, this invention is not bound by any theory, but it is believed that a high degree of vacuum may be required to remove bulk solvent from cholinesterase (particularly eel cholinesterase) at temperatures close to or below the normal ambient range, e.g. below 35° C. To provide further protection against deterioration of the enzyme, it is generally desirable that the vacuum drying/desiccation step be carried out at ordinary room temperature (e.g. 20°–25° C.) or lower, but preferably above the triple point of water (about 0.2° C.), more preferably above 10° C. The preferred degree of vacuum is 0.01 mm Hg or less. In a day or two, at 20°–25° C./0.01 mm Hg, sufficient enzyme stability will ordinarily be obtained. There does not presently appear to be any significant commercial advantage in extending the in-vacuo treatment beyond 48 hours, and some improvement in stability can be obtained in as little as one hour. The optimum duration of the treatment at 25° C. appears to be about 5 to about 20 hours at 0.01 mm Hg or less in a vacuum desiccator. To insure the full effectiveness of the in-vacuo treatment, a porous material impregnated with the enzyme is preferably allowed to air dry for two to three hours at room temperature (e.g. 20°–25° C.) before vacuum desiccation. To further insure the effectiveness of the vacuum step, dried air can be admitted to the vacuum desiccator before removing the desiccator lid, and the thus-dried impregnated porous material can be stored in sealed containers under refrigeration at 0°–10° C. (e.g. 5° C.) inside a second container provided with a desiccant material. It is also desirable to store porous material impregnated with the ester substrate or developer in tightly sealed containers inside of separate desiccated containers inside a refrigerator.

In carrying out vacuum desiccation or storage in the presence of a desiccant, materials with a high affinity for water can be used, e.g. $P_2O_5$, magnesium perchlorate, BaO, and other materials with a generally equally strong affinity for water.

MANUFACTURE OF DETECTOR KITS

In uniformly distributing the cholinesterase through the buffered aqueous medium, the cholinesterase can be in the form of a solid, a solution, dispersion, suspension, or the like. The buffering agent is preferably added to the aqueous medium prior to introducing the cholinesterase, so that the pH of the aqueous medium will be stabilized in the desired range at the outset; however, any sequence of addition consonant with the objective of uniformly distributing the cholinesterase through a buffered aqueous medium can be used. The activity of the enzyme in solution changes with the age of the solution; accordingly, if this activity is to be determined or standardized, a standard period of time prior to analysis is preferably observed. For example, the freshly prepared, buffered enzyme solution can be refrigerated at 5° C. for two to three hours prior to analysis.

The analysis for enzyme activity is carried out in accordance with the titration technique described previously. This technique involves the preparation of essentially three solutions: (a) a standardized substrate solution containing an ester which can be hydrolyzed readily with the aid of the enzyme, (b) a standardized enzyme solution, and (c) a standardized sodium hydroxide solution to be used as the titration agent.

To prepare one liter of substrate solution, the following are dissolved in about 900 ml of deionized water brought to a pH of 5.5:

8.120 g magnesium chloride hexahydrate (0.04 mole),
5.850 g sodium chloride (0.10 mole),
0.730 g acetylcholine chloride (0.004 mole).

Sufficient deionized water of pH 5.5 is added to bring the total volume up to 1.0 liter (1.0 cubic decimeter). This solution is stable for ten days if kept refrigerated at 5° C.

A suitable enzyme solution is prepared by dissolving approximately 100 units/mg in 30 ml of buffer solution. A suitable eel cholinesterase is obtainable from Worthington Biochemical Company. Forty ml of buffer solution can be prepared by suspending 6.60 g of 1,4-bis(3-sulfopropyl) piperazine or other buffer such as 1,4-bis(3-sulfo-2-hydroxypropyl)piperazine in 30 ml of deionized water, adjusting the pH to 8.0 using 5 M sodium hydroxide, and adding 0.20 g bovine serum albumin (0.5%), 0.6 ml 1.0% "TRITON X-100" solution, and sufficient additional deionized water to provide 40 ml of buffered aqueous medium. ("TRITON X-100" is a trademark for octylphenoxy polyethoxy ethanol nonionic wetting agent, which is available in essentially 100% concentration and has an HLB value of 13.5.)

The standardized 0.02 N sodium hydroxide solution can be prepared in any suitable conventional manner.

The analysis of the buffered enzyme solution is carried out in a ground-glass-bottom beaker with standard titration apparatus for dropwise addition of the standardized sodium hydroxide solution. Fifty milliliters of the substrate solution are pre-incubated in a 37° C. water bath for about 10 minutes, and then 0.100 ml of the enzyme solution is added with stirring to the substrate solution to initiate the hydrolysis. The titration is also initiated, using dropwise addition of the sodium hydroxide, and the rate of neutralization of the sodium hydroxide is observed and recorded for about 5 to 10 minutes. A linear titration versus time curve is obtained, from which the enzyme activity can be calculated as described previously.

To provide an impregnated porous material containing the enzyme, small discs or squares of ion exchange paper can be impregnated with the enzyme solution. A preferred size for a disc is 10–15 mm in diameter, which can readily absorb about 30 microliters of the enzyme solution. As noted previously, the total units of enzyme in the impregnated disc will be determined by the milligrams of enzyme used to make the solution multiplied by the assayed activity of the enzyme in units/mg. Greater amounts of enzyme solution (e.g. 40 microliters) per disc can be used, if desired.

As noted previously, the impregnated disc is allowed to air dry for two to three hours at room temperature before it is subjected to the desiccation in vacuo.

The procedure to be followed for making a horse serum cholinesterase disc is substantially the same as that for the eel cholinesterase disc, except that a different surfactant is preferred for the buffer solution. The amount of horse serum cholinesterase used to make an enzyme disc or square will be somewhat different, depending upon the activity of this type of cholinesterase. In any event, horse serum cholinesterase discs of 10–15 mm diameter are preferably designed to have an activity of 0.1–5 units per disc (e.g. 0.4 unit/disc).

The preparation of substrate discs or squares from filter paper and substrate solutions is relatively straightforward.

The "ticket" (described subsequently) for an extremely simple anticholinesterase detection kit can be made from a single enzyme disc, a single substrate disc, and suitably washed and desiccated polymeric sheeting. The preferred polymer sheets or films are relatively inert and hydrophobic and suitable for heat-sealing at moderate temperatures, e.g. below 120° C., preferably near 100° C. Synthetic organic polymers with good transparency, toughness, and flexibility are particularly desirable, particularly as compared to polymers which become brittle and may fracture at ordinary ambient winter temperature conditions (e.g. −20 to 10° C.). Heat-sealable polyolefins and other hydrophobic thermoplastic polymers are particularly well suited for fabrication of this element of the detector kit. A generally rectangular piece of the polymeric film can be cut to form a base for the discs. This base is preferably provided with a transverse crease or score which permits folding of the base upon itself. That is, the base (which resembles a large "ticket") can be folded in half so that one half is superimposed upon the other half. With the base unfolded and facing upward, a substrate disc is placed on one half and an enzyme disc upon the other half. A thermoplastic film overlay having approximately the same area as the bse can then be heat-sealed to the base, covering the discs and providing a moisture barrier which keeps the substrate disc and the enzyme disc in separate, hermetically sealed environments. The resulting completed enzyme/substrate "ticket" can be further packaged in a bag made from laminated foil packaging material along with an appropriately-sized piece of silica gel paper which has been freshly activated by heating to 150° C. for at least two hours. The bag can then be sealed shut with heat. If desired, the "ticket" which is inserted in the bag can be provided with one or more free tabs or tear strips which can facilitate removal of the overlay from the base, thereby exposing the enzyme disc and the substrate disc.

Use of the Detector Kit

The enzyme ticket package can be opened by tearing, thus permitting removal of the enzyme/substrate "ticket". The enzyme disc is then exposed, so that it is exposed to the environment or sample which is to be tested for an anticholinesterase agent. Moisture can be deliberately added to the enzyme disc, if necessary. Next the portion of the overlay over the substrate disc is removed and the wet enzyme disc and substrate disc can be pressed together for two minutes, e.g. using the thumb forefinger. After a time sufficient to develop the color change, the two discs can be pulled apart and the enzyme disc can be examined for color. Even a trace of color (e.g. the blue color characteristic of the indoxyl acetate color change) can be an indication that the enzyme is still active and that less than the threshold of inhibitor has been sampled.

For testing of the air, the enzyme disc in the exposed ticket can be exposed to either a stream of air, to ambient air, or to a sample of water which has been in intimate contact with the air. To test water, the ticket can be simply dipped in the water to be tested for a pre-determined time; the time would be varied in accordance with the desired sensitivity of the test. Generally a minute or two of exposure to the water would be sufficient, but greater sensitivies can be obtained by longer incubation times, i.e. longer periods of contact between the ticket and the water to be tested. For soil testing, the soil can be mixed with a small volume of water and allowed to settle. The supernatant can then be added to the enzyme disc portion of the ticket, as in the water test. For relatively clean surfaces such as leaves which have been sprayed with pesticides, it can be sufficient to wet the enzyme portion of the ticket with water and then press the leaf against the enzyme disc for a pre-determined time.

The sensitivity of the enzyme/substrate ticket for enzyme inhibitors is a function of the affinity of the enzyme for the enzyme inhibitor, the quantity of the enzyme on the enzyme ticket, the type of enzyme used on the enzyme ticket, the incubation time of the enzyme disc with the inhibitor, the temperature, and similar factors. It is possible to detect organophosphate compounds such as "SARIN" in water at the level of 0.02 mg/liter of water with a two-minute incubation time of the enzyme and the inhibitor. As will be apparent from the foregoing discussion, tickets can be tailored to meet the sensitivities required for specific applications.

The following non-limiting Examples illustrate the principle and practice of this invention.

EXAMPLE 1

Eel Cholinesterase/Indoxyl Acetate Detector Kit

In accordance with the procedures described previously, 10 mg of eel cholinesterase (Code ECH, Worthington Biochemical Company, approximately 100 units/mg) is dissolved in 30 ml of the 0.5 M, pH 8.0, "TRITON X-100"-containing 1,4-bis(3-sulfopropyl) piperazine buffer solution described previously. Then 30 microliters of the resulting buffered eel cholinesterase solution (i.e. 1.0 unit of the enzyme) were impregnated into 12.7 mm discs of DE81 (diethylaminoethyl ion exchange paper, 3.5 microequivalents per $cm^2$) paper (DEAE) discs, allowed to air-dry for 3 hours at room temperature, placed in uncapped glass vials and allowed to dry for 12 hours at 0.01 mm Hg, at 25° C. in a vacuum desiccator. Indoxyl acetate discs were prepared from the following solution and 9.0 cm Whatman No. 1 filter paper circles.

100 ml deionized water, pH 5.5
0.0448 g potassium ferricyanide
0.0715 g potassium ferrocyanide trihydrate One ml of the above solution was impregnated into each 9-centimeter filter paper circle and allowed to air-dry for 3 hours. Then an acetone solution of indoxyl acetate (18 mg/ml) was added to the dried filter paper, also in the amount of 1.0 ml per circle. The thus-impregnated filter paper was allowed to air-dry for 30 minutes, before being cut into 12.7 mm discs, under subdued light.

A 12.7 mm enzyme-treated (DEAE) disc and a 1.7 mm indoxyl acetate substrate disc were incorporated in an enzyme/substrate ticket as described previously. The thermoplastic sheeting was 20-mil (0.5 mm) polyethylene film. Prior to assembling the "ticket" from the discs, the polymer film base, and the polymer film overlay, the base and the overlay were washed in an alkyl aryl sodium sulfonate-containing ultrasonic cleaning bath, rinsed in deionized water, dried in an oven, and degassed in a desiccator.

EXAMPLE 2

The procedure of Example 1 was followed exactly with a buffered eel cholinesterase solution identical to that of Example 1, with the exception of the substitution of 0.5 M 1,4-bis(3-sulfo-2-hydroxypropyl) piperazine for 0.5 M 1,4-bis(3-sulfopropyl) piperazine. It was found that the 3-sulfopropyl and 3-sulfo-2-hydroxypropyl analogs were substantially equivalent.

The procedure of Example 1 was also repeated successfully with 1.7 $\mu$eq./$cm^2$ DEAE discs and with a different amine (cationic) ion exchange paper known at Whatman's ECTEOLA, a product formed by the reaction of cellulose with epichlorohydrin and triethanolamine.

EXAMPLE 3

Horse Serum Cholinesterase/Dichloroindophenyl Acetate Detector Kit

The horse serum cholinesterase was found to have an activity of approximately 15 units/g. Fifty-five milligrams of this cholinesterase were dissolved in 30 ml of an N-tris(hydroxymethyl) methyl-2-aminoethane sulfonic acid buffer solution essentially similar to that of Example 1 except for the use of 1 ml of 1% diester of sodium sulfosuccinic acid in place of "TRITON X-100" (octylphenoxy polyethoxy ethanol). The substrate discs were impregnated with 2,5-dichloroindophenyl acetate (DCIPA). To each 9.0 cm circle of filter paper there was added 1 ml of the DCIPA solution, which contained 5.0 mg/ml. The thus-impregnated filter paper circles were allowed to air-dry for about 1 hour under subdued light, cut into 12.7 mm discs, and vacuum dried following the same procedure for enzyme discs.

In this as in the preceding Examples, the silica gel desiccant for the kit can be activated for 2 or more hours at 150° C. and the laminated foil container chosen for its compatibility with the enzyme and its moisture barrier properties. A suitable laminated container is Continental Can Company's Retort Pouch which was used on the Apollo mission for food packaging. The enzyme tickets are stable in heat-sealed bags of this laminated material. Other laminated materials which include a metal foil (e.g. aluminum foil) as a highly effective moisture barrier are also useful and are typically more effective than polymeric film by itself.

What is claimed is:

1. A method for providing a treated porous material impregnated with a substantially stabilized cholinesterase comprising the steps of:
   (a) uniformly distributing the cholinesterase through an aqueous medium buffered to a pH greater than about 6 but less than about 9 with a buffering amount of a zwitterionic buffering agent,
   (b) impregnating a porous material with the aqueous medium containing said cholinesterase, and
   (c) drying the resulting impregnated porous material to remove substantially all of the physically bound water and thereby provide said treated porous material, having substantially no measurable water vapor pressure in a closed system.

2. A method according to claim 1 wherein the cholinesterase is electric eel cholinesterase.

3. A method of making an anticholinesterase detector kit comprising the steps of:
   (a) providing a treated porous material according to claim 2,
   (b) providing a second, separate porous material impregnated with an ester substrate for the substantially stabilized cholinesterase contained in said treated porous material,
   (c) packaging said treated porous material and said second, separate porous material in a package containing a barrier for preventing contact between said treated porous material and said second, separate porous material until detection of an anticholinesterase is attempted.

4. An anticholinesterase detector kit made according to claim 3.

5. A method for detecting environmental cholinesterase-inhibiting amounts of an anticholinesterase with the detector kit of claim 3 comprising the steps of:
   (a) exposing said treated porous material to the environment, and
   (b) removing said barrier between said treated porous material and said second, separate porous material and bringing said treated porous material and said second, separate porous material into contact.

6. A method according to claim 3, wherein the zwitterionic buffering agent for the cholinesterase is an 0.5 molar solution of a compound selected from the group consisting of 1,4-bis(3-sulfo-2-hydroxypropyl) piperazine and 1,4-bis(3-sulfopropyl) piperazine.

7. A method for detecting the presence of a cholinesterase-inhibiting amount of an ambient cholinesterase inhibitor comprising the steps of:
(a) providing a treated porous material according to claim 2,
(b) exposing said treated porous material to the ambient conditions, and
(c) contacting said treated porous material with an ester substrate for said substantially stabilized cholinesterase.

8. A method for providing a treated porous material impregnated with a substantially stabilized electric eel cholinesterase comprising the steps of:
(a) uniformly distributing the cholinesterase through an aqueous medium buffered to a pH greater than about 6 but less than about 9 with a buffering amount of a zwitterionic buffering agent,
(b) impregnating a porous material with the aqueous medium containing said cholinesterase, and
(c) subjecting the resulting impregnated porous material to a partial vacuum for at least 1 hour in a zone of subatmospheric pressure and generally normal ambient temperature; the pressure in said zone being less than 1.0 mm of mercury; thereby obtaining said treated porous material.

9. A method according to claim 8 wherein:
(a) said zwitterionic buffering agent comprises a compound comprising a sulfonic acid group and a protonatable amine group,
(b) said porous material is a sheet-like material having only two major surfaces, and
(c) said pressure in said zone is less than 0.1 mm of mercury, and said porous substrate is subjected to said partial vacuum for about 1–48 hours.

10. A method according to claim 9 wherein:
said zwitterionic buffering agent comprises a substantially water soluble compound of the formula

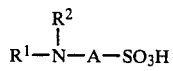

wherein A represents a divalent aliphatic, heterocylcic or carbocyclic aliphatic, or aromatic group, and
$R^1$ and $R^2$ are the same or different and represent carbocyclic or heterocyclic aliphatic, aliphatic, or aromatic groups, or $R^1$ and $R^2$ can together constitute the residue of a carbocyclic or heterocyclic cycloaliphatic or aromatic ring.

11. A method according to claim 10 wherein said zwitterionic buffering agent is selected from the group consisting of the substantially water-soluble 1,4-bis(sulfoalkyl) piperazines, 1,4-bis(sulfohydroxyalkyl) piperazines, omega-monoaminoalkyl sulfonic acids, and combinations thereof.

12. A method according to claim 11, wherein the zwitterionic buffering agent for the cholinesterase is an 0.5 molar solution of a compound selected from the group consisting of 1,4-bis(3-sulfo-2-hydroxypropyl) piperazine and 1,4-bis(3-sulfopropyl) piperazine.

13. A method according to claim 10 wherein said aqueous medium buffered with said zwitterionic buffering agent comprises a 0.01–1.0 molar solution of said zwitterionic buffering agent.

14. A method of any of claims 1 or 3 in which the porous substrate is an ion exchange paper.

15. A method for providing a treated porous material impregnated with a substantially stabilized electric eel cholinesterase comprising the steps of:
(a) uniformly distributing the cholinesterase through an aqueous medium buffered to a pH greater than about 6 but less than about 9 with a buffering amount of a zwitterionic buffering agent,
(b) impregnating a porous material with the aqueous medium containing said cholinesterase, and
(c) subjecting the resulting impregnated porous material to a partial vacuum in a zone of subatmospheric pressure and generally normal ambient temperature; the pressure in said zone being less than 1.0 mm of mercury; thereby removing substantially all physically bound water from the resulting dried electric eel cholinesterase, the water vapor pressure of said dried electric eel cholinesterase being substantially unmeasurable in a closed system.

16. An anti-cholinesterase detector kit, said kit consisting essentially of the following components contained within a moisture resistant package:
(a) an extremely dry, impregnated porous material, said porous material being impregnated with cholinesterase and a buffering amount of a zwitterionic buffering agent, said impregnated porous material being dried by subjecting the resulting impregnated porous material to a partial vacuum for at least 1 hour in a zone of subatmospheric pressure and generally normal ambient temperature; the pressure in said zone being less than 1.0 mm of mercury;
(b) a dry ester substrate for the cholinesterase, said substrate being separated from the cholinesterase by a barrier for preventing cholinesterase inactivation by sublimation of the substrate during storage.

17. A kit of claim 16 in which the porous material is an ion exchange paper.

18. A kit of claim 17 in which the dry impregnated ion exchange paper has been dried so that it has substantially no measurable water vapor pressure in a closed system.

19. A kit of claim 18 in which the cholinesterase and the ester substrate are supported on a common base which can be folded against itself so that the cholinesterase and substrate can contact each other when the barrier that separates them is removed.

* * * * *

UNITED STATES PATENT AND TRADEMARK OFFICE
CERTIFICATE OF CORRECTION

PATENT NO. : 4,324,858
DATED : April 13, 1982
INVENTOR(S) : Louis H. Goodson and Alan Goodman It is certified that error appears in the above-identified patent and that said Letters Patent are hereby corrected as shown below:

In Abstract, lines 14 and 15, for "pollutant" read
  --pollutants--.
In Abstract, line 15, for "organophosphorous" read
  --organophosphorus--.
Column 2, line 43, for "a" read --at--.
Column 3, line 31, for "Hq" read --Hg--.
Column 4, line 57, for "2ethyl" read --2-ethyl--.
Column 4, line 63, for "÷" read --"--.
Column 4, line 66, for "'GP'" read --"GB"--.
Column 5, line 64, for "aminol" read --amino--.
Column 7, line 17, for "sits" read --sites--.
Column 7, line 35, for "sterospecific" read
  --stereospecific--.
Column 9, line 68, for "bse" read --base--.
Column 10, line 27, for "thumb forefinger" read
  --thumb and forefinger--
Column 11, line 52, for "at" read --as--.
Column 13, line 44, for "cylcic" read --cyclic--.

Signed and Sealed this

Twenty-fifth Day of January 1983

[SEAL]

Attest:

GERALD J. MOSSINGHOFF

Attesting Officer    Commissioner of Patents and Trademarks

UNITED STATES PATENT AND TRADEMARK OFFICE
CERTIFICATE OF CORRECTION

PATENT NO. : 4,324,858

DATED : April 13, 1982

INVENTOR(S) : Louis H. Goodson and Alan Goodman

It is certified that error appears in the above-identified patent and that said Letters Patent is hereby corrected as shown below:

Column 1, Line 6, after "STABILIZATION OF CHOLINESTERASE, DETECTOR KIT USING STABILIZED CHOLINESTERASE, AND METHODS OF MAKING AND USING THE SAME," and before "TECHNICAL FIELD" please insert --The Government has rights in this invention pursuant to Contract DAAA15-76-C-0132 awarded by the U.S. Army Armament Research and Development Command. The invention described herein may be manufactured, used, and licensed by or for the Government for governmental purposes without the payment to use of any royalty thereon.--

Signed and Sealed this

Nineteenth Day of August 1986

[SEAL]

*Attest:*

DONALD J. QUIGG

*Attesting Officer*  *Commissioner of Patents and Trademarks*